(12) United States Patent
Kim et al.

(10) Patent No.: US 9,950,186 B2
(45) Date of Patent: Apr. 24, 2018

(54) PHOTOTHERAPY DISPLAY DEVICE AND METHOD FOR CONTROLLING THE SAME

(71) Applicant: SAMSUNG DISPLAY CO., LTD., Yongin-si, Gyeonggi-do (KR)

(72) Inventors: Kwang Jun Kim, Seoul (KR); Hwang Keun Kim, Seoul (KR); Yong-Han Park, Hwaseong-si (KR); Jong Sung Bae, Hwaseong-si (KR); Dong Ho Lee, Suwon-si (KR); Young-Cheol Jeong, Hwaseong-si (KR)

(73) Assignee: SAMSUNG DISPLAY CO., LTD. (KR)

( * ) Notice: Subject to any disclaimer, the term of this patent is extended or adjusted under 35 U.S.C. 154(b) by 161 days.

(21) Appl. No.: 14/939,814

(22) Filed: Nov. 12, 2015

(65) Prior Publication Data
US 2016/0136449 A1 May 19, 2016

(30) Foreign Application Priority Data
Nov. 14, 2014 (KR) .................... 10-2014-0158972

(51) Int. Cl.
*A61N 5/06* (2006.01)
*G06T 5/00* (2006.01)
*A61M 21/00* (2006.01)

(52) U.S. Cl.
CPC ............ *A61N 5/06* (2013.01); *A61M 21/00* (2013.01); *G06T 5/002* (2013.01);
(Continued)

(58) Field of Classification Search
CPC .......... G06T 5/002; G06T 2207/20172; A61M 21/00; A61M 2021/0044; A61M 2205/505; A61N 2005/0626; A61N 5/06
See application file for complete search history.

(56) References Cited

U.S. PATENT DOCUMENTS 6,147,792 A * 11/2000 Jones ................. G09G 3/20
345/51
2003/0025656 A1* 2/2003 Kimura ............... G09G 3/3258
345/82
(Continued)

FOREIGN PATENT DOCUMENTS

JP 2006-231057 A 9/2006
JP 2011-072388 A 4/2011
(Continued)

OTHER PUBLICATIONS

George C. Brainard et al., "Action Spectrum for Melatonin Regulation in Humans: Evidence for a Novel Circadian Photoreceptor," The Journal of Neuroscience, Aug. 15, 2001, pp. 6405-6412, vol. 21(16), Society for Neuroscience, U.S.A.
(Continued)

*Primary Examiner* — Gregory J Tryder
*Assistant Examiner* — Michael Le
(74) *Attorney, Agent, or Firm* — Innovation Counsel LLP

(57) ABSTRACT

According to one aspect, a display device may include: a display unit including a plurality of pixels; and a controller arranged to receive an image signal comprising a plurality of image frames and then, if certain of the image frames are determined to represent a still image, to insert a sub-image frame between immediately successive image frames of the certain of the image frames, the sub-image frame allowing at least one of the plurality of pixels to emit light of a specified wavelength.

20 Claims, 6 Drawing Sheets

(52) U.S. Cl.
CPC .............. *A61M 2021/0044* (2013.01); *A61M 2205/505* (2013.01); *A61N 2005/0626* (2013.01); *G06T 2207/20172* (2013.01)

(56) References Cited

U.S. PATENT DOCUMENTS

| | | | | |
|---|---|---|---|---|
| 2007/0296660 | A1* | 12/2007 | Kimura | G09G 3/20 345/87 |
| 2009/0179848 | A1* | 7/2009 | Schmidt | G09G 3/2081 345/102 |
| 2012/0293564 | A1* | 11/2012 | Kajiyama | G09G 3/2022 345/690 |
| 2013/0046212 | A1 | 2/2013 | Nichols | |
| 2014/0204132 | A1* | 7/2014 | Akimoto | G09G 3/2022 345/691 |
| 2014/0313245 | A1 | 10/2014 | Park et al. | |
| 2015/0217130 | A1 | 8/2015 | Gross et al. | |

FOREIGN PATENT DOCUMENTS

| | | |
|---|---|---|
| JP | 2015-196076 A | 11/2015 |
| KR | 10-1995-0030611 A | 11/1995 |
| KR | 10-2005-0074946 A | 7/2005 |
| KR | 10-2009-0019905 A | 2/2009 |
| KR | 10-2011-0092630 A | 8/2011 |
| KR | 10-2012-0052754 A | 5/2012 |

OTHER PUBLICATIONS

Helen R. Wright et al., "Light Emitting Diodes can be Used to Phase Delay the Melatonin Rhythm," Journal of Pineal Research, Feb. 26, 2001, pp. 350-355, ISSN 0742-3098, Munksgaard, Ireland.

C-C.E. Lan et al., "Low-Energy Helium-Neon Laser Induces Melanocyte Proliferation via Interaction with Type IV Collagen: Visible Light as a Therapeutic Option for Vitiligo," British Journal of Dermatology, Feb. 23, 2009, pp. 273-280, vol. 161, British Association of Dermatologists, London.

Daniel Barolet, MD, "Light-Emitting Diodes (LEDs) in Dermatology," Seminars in Cutaneous Medicine and Surgery, Dec. 2008, pp. 227-238, vol. 27, Elsevier Inc.

Tetsuo Katsuura et al., "Effects of Blue Pulsed Light on Human Physiological Functions and Subjective Evaluation," Journal of Physiological Anthropology, Sep. 2012, pp. 1-5, vol. 31:23, distributed under the terms of the Creative Commons Attribution License.

Jihao Yin et al., "Optimal Band Selection for Hyperspectral Image Classification Based on Inter-Class Separability," IEEE, Jun. 2010, 4 pages, vol. 10, IEEE.

European Search Report for European Patent Application No. 15194245.5, European Patent Office, dated Mar. 29, 2016, 7 pages, Munich, Germany.

* cited by examiner

PHOTOTHERAPY DISPLAY DEVICE AND METHOD FOR CONTROLLING THE SAME

CROSS-REFERENCE TO RELATED APPLICATION

This application claims priority to, and the benefit of, Korean Patent Application No. 10-2014-0158972 filed in the Korean Intellectual Property Office on Nov. 14, 2014, the entire contents of which are incorporated herein by reference.

BACKGROUND (a) Technical Field

The described technology generally relates to flat panel display devices, and more specifically relates to a display device and associated control methods for facilitating treatment of a disease or disorder using light.

(b) Discussion of the Background

Light exposure methods have been developed recently, for treatment of diseases or disorders. These treatment methods include a method of exposing a patient to light of a specific wavelength band, and a method of exposing a patient to light in combination with a drug therapy. Such treatment methods are typically referred to as a phototherapy.

Phototherapy has been used, for example, for treatment of diseases such as jaundice of the newborn, acne, psoriasis, eczema, cancer, neurological disorders, seasonal affective disorder, depression, bulimia, hand tremor associated with Parkinson's disease, ulcers, and circadian rhythm maintenance disorders as well as other diseases, disorders, or illnesses. Phototherapy has been used to promote injury recovery, to promote relaxation, to improve fertility, to stimulate hair growth, and to reduce expression of cellulite and wrinkles.

Some phototherapy devices have been developed for treatment of a specific disease. In general, these phototherapy devices are designed to transmit specifically controlled light to the patient. The phototherapy devices may use fluorescent lamps, halogen lamps, inorganic or organic light emitting diodes as a direct spot light, or in combination with optical fibers.

The effectiveness of phototherapy is generally dependent on the intensity of light used, a surface area exposed to light, and a percentage of a light spectrum that includes an effective wavelength for treatment of diseases or disorders.

The above information disclosed in this Background section is only for enhancement of understanding of the background and therefore it may contain information that does not form the prior art that is already known in this country to a person of ordinary skill in the art.

SUMMARY

Embodiments of the present invention help to solve the aforementioned problems and other problems by providing a display device and a control method therefor, for enabling treatment of a specific disease or disorder by using light, and by providing a display device and a control method therefor for reducing distortion of a display image due to phototherapy.

According to one aspect, a display device may include: a display unit including a plurality of pixels; and a controller arranged to receive an image signal comprising a plurality of image frames. If the certain of the image frames are determined to represent a still image, the controller is arranged to insert a sub-image frame between immediately successive image frames of the certain of the image frames, the sub-image frame allowing at least one of the plurality of pixels to emit light of a specified wavelength.

The controller may be further constructed to separate a first one of the image frames into a plurality of sub-images, compare the plurality of sub-images with corresponding sub-images of a previous one of the image frames that is received before the first image frame, detect whether the compared sub-images differ from each other, and thereby determine whether the image signal represents the still image signal.

The display device may further include a memory storing information corresponding to the specified wavelength of light to be emitted.

The controller may be further arranged to receive a control signal for controlling insertion of the sub-image frame, and may read the information from the memory according to the control signal.

The plurality of image frames may include immediately successive first and second image frames, and the controller may be further constructed to insert the sub-image frame such that an interval between the first image frame and the sub-image frame is greater than that between the sub-image frame and the second image frame.

The control signal may include a signal directing the controller to selectively read the information corresponding to the specified wavelength.

The controller may be further constructed to correct a color of the image signal at least partially according to the specified wavelength of the sub-image frame that is selected by the control signal.

The controller may be further constructed to correct the color of the image signal at least partially according to a ratio of the interval between the first image frame and the sub-image frame to the interval between the sub-image frame and the second image frame.

The memory may further store information corresponding to a color correction matrix for correcting the color of the image signal.

The controller may be further constructed to read the information, and to insert ones of the sub-image frames between successive image frames.

The control signal may include a signal for directing the controller such that the sub-image frame for emitting light of a wavelength corresponding to a specific time zone is displayed.

A method of controlling a display device includes: receiving an image signal; determining whether the image signal represents a still image; and inserting, if the image signal is determined to represent a still image, a sub-image frame between immediately successive image frames, the sub-image frame allowing at least one of the plurality of pixels to emit light of a specified wavelength.

The determining may further include: separating a first one of the image frames into a plurality of sub-images; and detecting whether the sub-images of successive image frames represent a still image, by comparing the sub-images of the first one of the image frames with the corresponding sub-images of a previous image frame.

The method may further include: receiving a control signal for controlling insertion of the sub-image frame; and reading, from a memory, information corresponding to a specified wavelength of light to be emitted according to the sub-image frame.

The inserting may further include inserting the sub-image frame between successive first and second ones of the image frames so that an interval between the first image frame and the sub-image frame is greater than an interval between the sub-image frame and the second image frame.

The reading may further include selectively reading the information from the memory.

The method may further include correcting a color of the image signal according to the specified wavelength corresponding to the selectively read information.

The correcting may further include correcting the color of the image signal at least partially according to a ratio of the interval between the first image frame and the sub-image frame to the interval between the sub-image frame and the second image frame.

The information may correspond to multiple ones of the specified wavelengths.

The inserting may further include respectively sequentially inserting multiple ones of the sub-image frames each between two immediately successive image frames.

At least one of the exemplary embodiments may advantageously reduce distortion of displayed images and aid in treat specific diseases or disorders.

An additional range of applicability will become clear from the following detailed description.

However, since various modifications and alternations within the spirit and scope may be clearly understood by those skilled in the art, it is to be understood that a detailed description and a specific exemplary embodiment such as an exemplary embodiment are provided only by way of example.

DETAILED DESCRIPTION OF THE EMBODIMENTS

Figure 1:
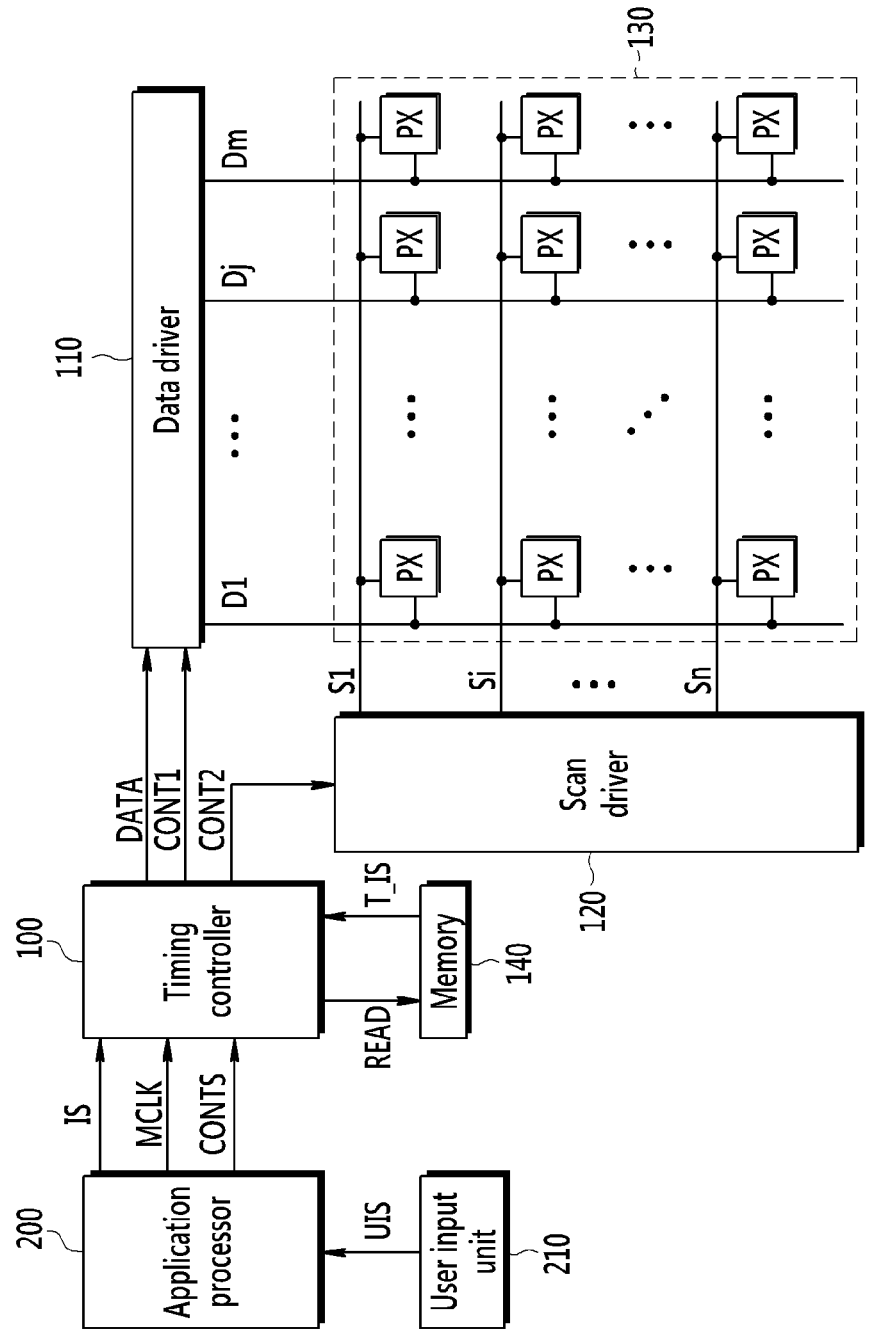
FIG. 1 is a block diagram of a display device related to an exemplary embodiment.

Hereinafter, exemplary embodiments disclosed in the present specification will be described in detail with reference to the accompanying drawings. In the present specification, the same or similar components will be denoted by the same or similar reference numerals, and an overlapped description thereof will be omitted.

Terms "module" and "unit" for components used in the following description are used only in order to easily make a specification. Therefore, these terms do not have meanings or roles that distinguish them from each other in themselves.

Further, in describing exemplary embodiments of the present specification, when it is determined that a detailed description of the well-known art associated with the present invention may obscure the gist of the present invention, such detailed description may be omitted.

In addition, the accompanying drawings are provided only in order to allow exemplary embodiments disclosed in the present specification to be easily understood and are not to be interpreted as limiting the spirit disclosed in the present specification, and it is to be understood that the present invention includes all modifications, equivalents, and substitutions without departing from the scope and spirit.

Terms including ordinal numbers such as first, second, and the like, will be used only to describe various components, and are not interpreted as limiting these components.

The terms are only used to differentiate one component from other components.

It is to be understood that when one component is referred to as being "connected" or "coupled" to another component, it may be connected or coupled directly to another component or be connected or coupled to another component with the other component intervening therebetween.

On the other hand, it is to be understood that when one component is referred to as being "connected or coupled directly" to another component, it may be connected to or coupled to another component without the other component intervening therebetween.

Singular forms are to include plural forms unless the context clearly indicates otherwise.

It will be further understood that terms "comprises" or "have" used in the present specification specify the presence of stated features, numerals, steps, operations, components, parts, or a combination thereof, but do not preclude the presence or addition of one or more other features, numerals, steps, operations, components, parts, or a combination thereof.

The various Figures are not to scale. All numerical values are approximate, and may vary. All examples of specific materials and compositions are to be taken as nonlimiting and exemplary only. Other suitable materials and compositions may be used instead.

A display device described in the present specification may include digital TVs, mobile phones, smartphones, laptop computers, digital broadcasting terminals, personal digital assistants (PDAs), portable multimedia players (PMPs), navigation devices, slate PCs, tablet PCs, ultrabooks, wearable devices (e.g., watch-type terminals (smart watches), glasses type terminals (smart glasses), head mounted displays (HMDs), desktop computers, digital signages, etc.

FIG. 1 is a block diagram of a display device related to the exemplary embodiment. Referring to FIG. 1, the display device includes a display unit 130 including a plurality of pixels PX, a scan driver 120, a data driver 110, a timing controller 100, and a memory 140. Further, the display device may be connected to an application processor 200. In addition, a user input unit 210 may be connected to the application processor 200. The application processor 200 and the user input unit 210 may be provided outside of the display device, or may be incorporated in the display device.

The constituent elements illustrated in FIG. 1 are not essential for embodiment of the display device, so the display device described in the present specification may include more or fewer constituent elements than those described above.

The display unit 130 is a display panel including a plurality of pixels PX that are connected to corresponding scan lines S1 to Sn and corresponding data lines D1 to Dm.

Each of the plurality of pixels PX displays an image in accordance with an image data signal that is transmitted to the corresponding pixels PX. The plurality of pixels PX included in the display unit 130 are respectively connected to the plurality of scan lines S1 to Sn and the plurality of data lines D1 to Dm, and are arranged in an approximate matrix form.

The plurality of scan lines S1 to Sn substantially extends in a row direction such that, in the embodiment shown, they are almost parallel to each other.

The data lines D1 to Dm substantially extend in a column direction such that, in this embodiment, they are almost parallel to each other.

The scan driver 120 is connected to the display unit 130 via the plurality of scan lines S1 to Sn. The scan driver 120 generates a plurality of scan signals for activating each pixel PX of the display unit 130 according to a scan control signal CONT2, and transmits the scan signals to the corresponding scan lines S1 to Sn.

The scan control signal CONT2 is a signal for controlling an operation of the scan driver 120, and is generated by the timing controller 100. The scan control signal CONT2 may include a scan start signal, a clock signal CLK (not shown but included in CONT2 in, for example, known manner), etc. The scan start signal is a signal for generating a first scan signal for displaying one frame of an image. The clock signal CLK is a synchronization signal for sequentially applying the scan signals to the plurality of scan lines S1 to Sn.

The data driver 110 is connected to each pixel PX of the display unit 130 via the plurality of data lines D1 to Dm. The data driver 110 receives an image data signal DATA and transmits it to the corresponding data lines D1 to Dm according to a data control signal CONT1.

The data control signal CONT1 is a signal for controlling an operation of the data driver 110, and is generated by the timing controller 100.

The data driver 110 selects a gray voltage according to the image data signal DATA, and transmits it as a data signal to the appropriate one of the data lines D1 to Dm.

The timing controller 100 may receive an image signal IS that is received from the application processor 200, an input control signal for controlling display of the image signal IS, and a phototherapy control signal CONTS.

The image signal IS contains luminance information about each pixel PX of the display unit 130, and luminance has a predetermined number of grays, for example, 1024, 256, or 64.

Examples of the input control signal transmitted to the timing controller 100 are a vertical synchronization signal, a horizontal synchronization signal, a main clock signal MCLK, a data enable signal, etc.

The timing controller 100 may display a phototherapy image on the display unit 130 according to the phototherapy control signal CONTS. In particular, the timing controller 100 may transmit a signal READ for reading the phototherapy image to the memory 140 and may also read a phototherapy image signal T_IS from the memory 140. The timing controller 100 may receive the image signal per frame and detect whether the image signal is a still image or not. Further, depending on whether the image signal is a still image or not, the timing controller 100 may generate a signal for controlling the phototherapy image to be displayed in the display unit 130.

More specifically, the timing controller 100 separates a current frame image of a current input image into a plurality of sub-images. In addition, the timing controller 100 compares the plurality of sub-images with corresponding sub-images of a previous frame image that is previously received, and detects whether each of the sub-images is different from its corresponding previous frame or not.

For example, the timing controller 100 separates the frame image included in the input image signal into two sub-images, i.e. first and second sub-images, compares a pixel value of one of the sub-images with that of the corresponding sub-image of the previous frame image, and determines whether the sub-image as the still image, i.e. a motionless image, if a difference between the two pixel values is below a predetermined threshold value. Likewise, the image is determined to be a moving image if the difference between the pixel values exceeds a predetermined threshold value.

If the sub-image is determined to be a still image, the timing controller 100 may read the phototherapy image signal T_IS from the memory 140, and mix it with the image signal to generate the image data signal DATA. Further, the timing controller 100 appropriately image-processes the image signal IS and/or the phototherapy image signal T_IS such that they meet an operating condition of (e.g., are in the proper format for) the display unit 130 and the data driver 110 based on the image signal IS, the phototherapy image signal T_IS, the input control signal, and the phototherapy control signal CONTS that are received.

Specifically, the timing controller 100 may generate the image data signal DATA by performing various image-processing processes on the image signal IS, such as gamma correction, luminance compensation, color correction, etc.

The timing controller 100 may generate the image data signal DATA such that the image according to the image signal IS and the image according to the phototherapy image signal T_IS are appropriately mixed and displayed. In addition, the timing controller 100 may correct a color of the image signal IS according to the phototherapy image signal T_IS. This will be described later with reference to FIG. 2.

In addition, the timing controller 100 transmits the scan control signal CONT2, for controlling the operation of the scan driver 120, to the scan driver 120.

The timing controller 100 generates the data control signal CONT1 for controlling the operation of the data driver 110, and transmits the data control signal CONT1 along with the previously image-processed image data signal DATA to the data driver 110.

The memory 140 stores color correction matrix values corresponding to a plurality of phototherapy image signals T_IS, and also stores each of the phototherapy images.

According to the phototherapy image signal T_IS that is read from the memory 140, the timing controller 100 may calculate the corresponding color correction matrix value with the image signal, to correct the color of the image signal.

The color correction matrix values are different depending on wavelengths of the respective phototherapy images.

When one image frame of the phototherapy image for displaying light of a specific wavelength is inserted between the image frames of the display image, a color mixture between the phototherapy image and the display image may occur. That is, affected by light of a specific wavelength, a patient (or user) may recognize the color of the display image as being distorted. In other words, the inserted phototherapy images may change the perceived color of the display image.

Thus, a color correction matrix value that depends on the wavelength of the phototherapy image is output to the timing controller 100, and is used to modify or compensate the image signal, thereby preventing distortion of the display image.

The memory 140 may include at least one of a flash memory, a hard disk, a solid state disk (SSD), a silicon disk drive (SDD), a micro-type multimedia card, a card-type memory (e.g., SD or XD memory), random access memory (RAM), static random access memory (SRAM), read-only memory (ROM), electrically erasable programmable read-only memory (EEPROM), programmable read-only memory (PROM), a magnetic memory, a magnetic disk, and an optical disk. Any form of information storage is contemplated.

The application processor 200 outputs the image signal IS, the input control signal, and the phototherapy control signal CONTS to the timing controller 100. While being connected to the user input unit 210, the application processor 200 may generate signals according to user-input information (UIS), and output the signals to the timing controller 100.

The application processor 200 may generate the phototherapy control signal CONTS according to the user-input information (UIS). For example, the application processor 200 may generate the phototherapy control signal CONTS such that the display unit 130 initiates display of the phototherapy image for displaying light of the specific wavelength. As another example, the application processor 200 may generate the phototherapy control signal CONTS such that the display unit 130 initiates display of the phototherapy image for displaying light of the specific wavelength according to a specific time zone.

The user input unit 210 (e.g., touch key, mechanical key, microphone, etc.) is designed for receiving information from a user, and transmits the user-input information (UIS) to the application processor 200. For example, the user input unit 210 may receive a gesture, a voice input, and a command input of a user who wants to display the phototherapy image on the display device. Then, the user input unit 210 may generate the corresponding user-input information (UIS) and transmit it to the application processor 200.

Exemplary embodiments related to a control method that can be realized in the display device configured as described above will now be described with reference to the accompanying drawings. Those skilled in the art will realize that the present invention may be modified in various different ways without departing from the spirit or desirable features disclosed herein.

Figure 2:
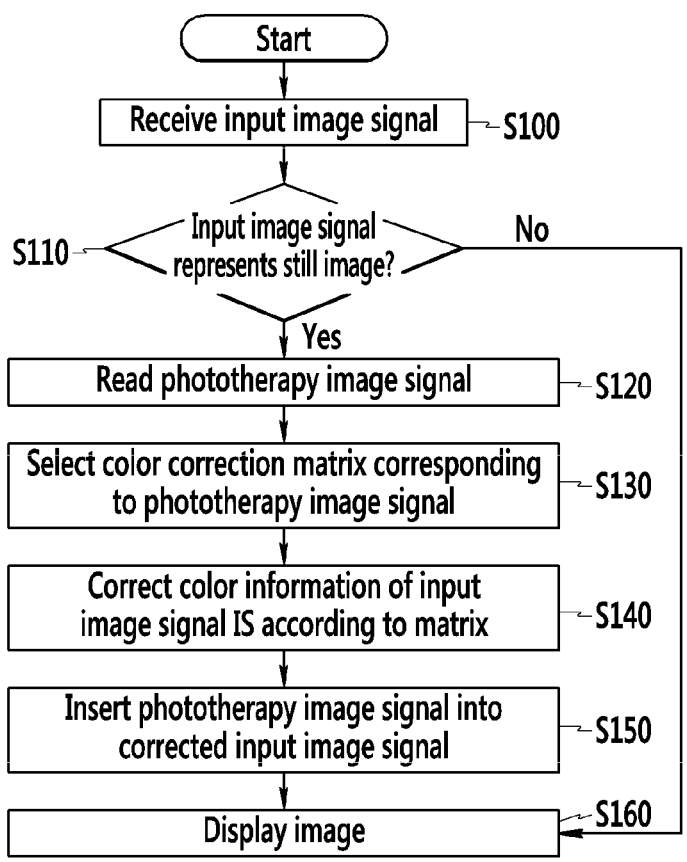
FIG. 2 is a flowchart illustrating a method for controlling the display device related to an exemplary embodiment.

FIG. 2 is a flowchart illustrating a method for controlling the display device. As described above, a timing controller 100 receives an input image signal IS from an application processor 200 (S100). Then, the timing controller 100 determines whether the input image signal represents a still image or not (S110). The timing controller 100 compares a pixel value of each of the sub-images of the current frame image with that of each of the corresponding sub-images of a previous frame image, and determines that the sub-image represents still image, which is a motionless image, if a difference between the pixel values is below a predetermined threshold value, and represents a moving image if the difference between the pixel values exceeds a predetermined threshold value.

Next, if the image signal is determined to be a still image, the timing controller 100 reads a phototherapy image signal T_IS from a memory 140 (S120). In this case, according to a phototherapy control signal CONTS that is received from the application processor 200, the timing controller 100 may read the phototherapy image signal T_IS for displaying light of a specific wavelength. The timing controller 100 may then select a color correction matrix corresponding to a phototherapy image from the memory 140 (S130), and may calculate the corrected or compensated input image signal IS using the color correction matrix (S140). For example, the timing controller 100 may correct the color of input image IS by multiplying the R, G, B vector component of input image IS by the color correction matrix.

The timing controller 100 may calculate the input image signal IS and the color correction matrix in consideration of a display time of the input image frame and a display time of the phototherapy image frame.

The timing controller 100 then inserts the phototherapy image signal T_IS into the corrected input image signal IS (S150). The timing controller 100 may insert the phototherapy image frame between the corrected input image frames. This will be described together with reference to FIGS. 3 and 4.

Figure 3:
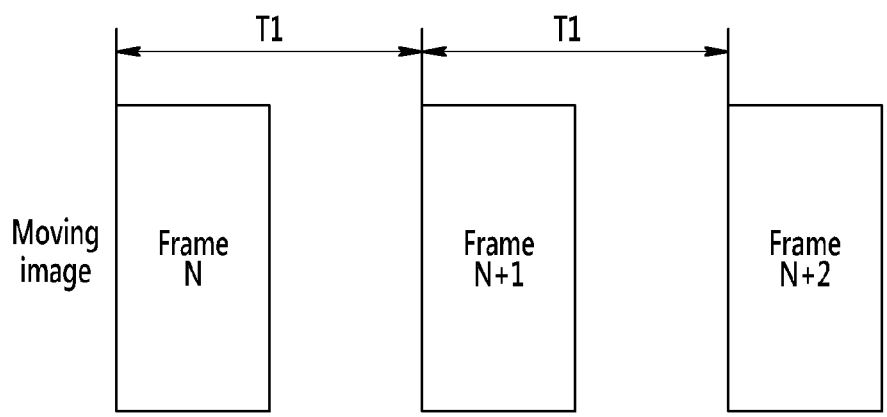
FIGS. 3 and 4 are drawings illustrating an example of inserting a phototherapy image into an input image according to an exemplary embodiment.
Figure 4:
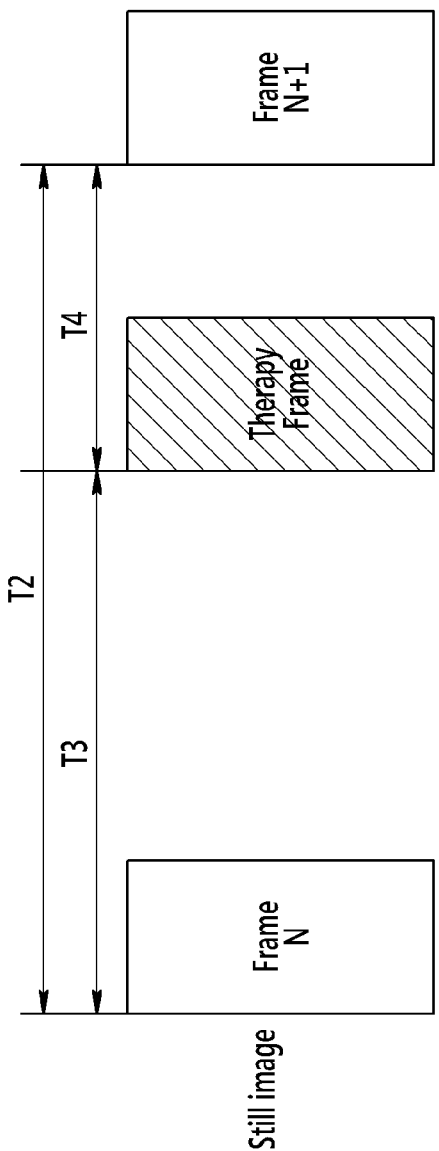

FIGS. 3 and 4 are drawings illustrating an example of inserting a phototherapy image into an input image according to an exemplary embodiment. As described in FIG. 3, when the input image signal IS is a moving image, a period for sequentially displaying a plurality of image frames may be T1. As shown in FIG. 4, when the input image signal IS is a still image, an interval between the image frames of the continuous still image may be a period T2 that is greater than period T1.

The phototherapy image frame may be inserted between the image frames of the still image. In particular, the phototherapy image frame is inserted between an N-th image frame and an (N+1)-th image frame of a still image.

An interval between the N-th image frame and the phototherapy image frame may be a period T3 that is greater than T1. Also, an interval between the phototherapy image frame and the (N+1)-th image frame may be a period T4 that is smaller than T3.

A color correction matrix may be calculated with the input image signal IS in consideration of a ratio of period T3 to period T4. For example, as a difference between periods T3 and T4 grows smaller, a display time of the phototherapy image frame increases. Then, a patient recognizes a color of the display image as being further distorted. Accordingly, an input matrix value when the difference between periods T3 and T4 is "a", is greater than that when the difference between periods T3 and T4 is "b" (a>b). The timing controller 100 outputs the signals such that the color-corrected input image frame, and the inserted phototherapy image frame, are sequentially displayed on the display unit 130 (S160).

Figure 5:
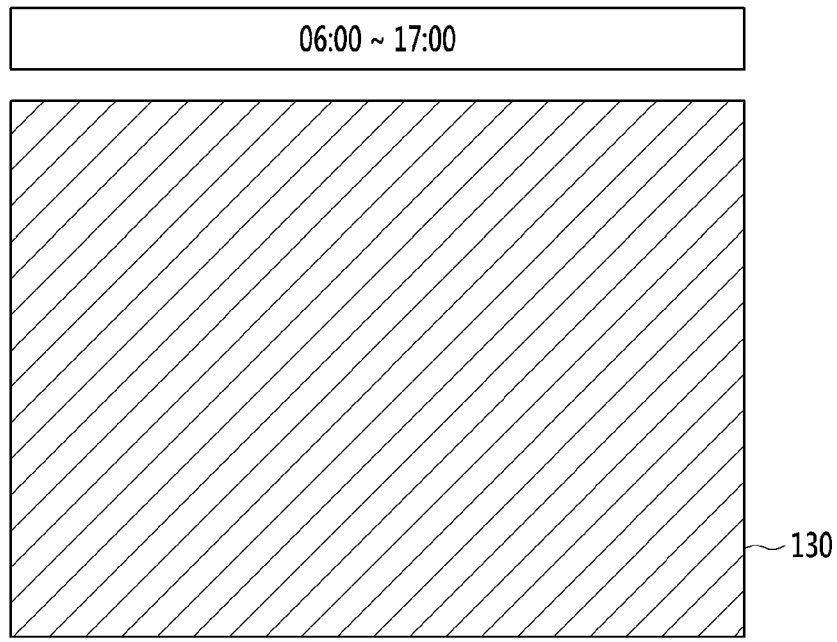
FIGS. 5 to 7 are drawings illustrating a method for controlling wavelengths of a phototherapy image according to another exemplary embodiment.
Figure 6:
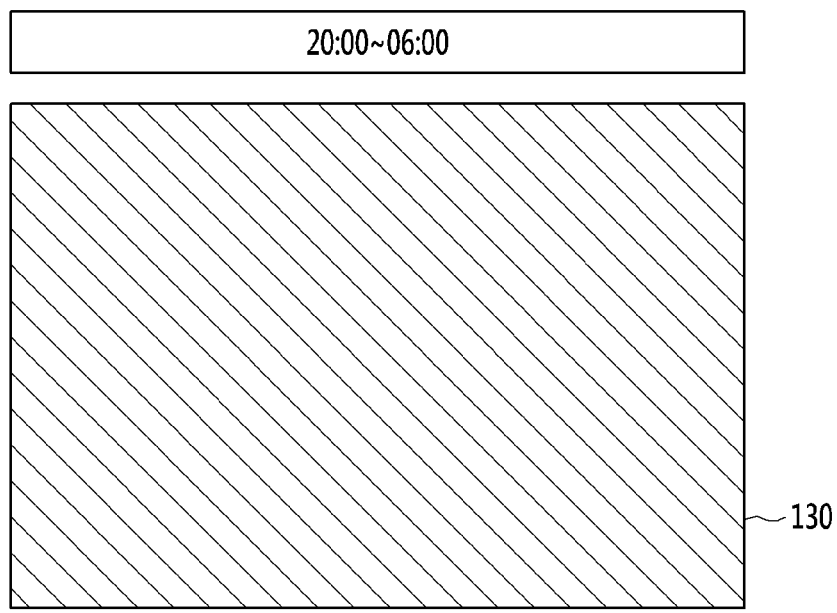
Figure 7:
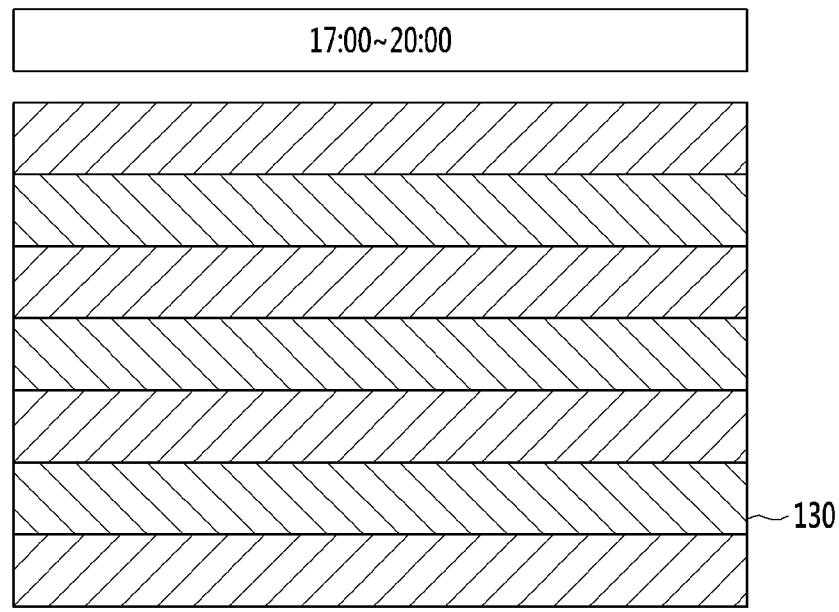

Next, a method of displaying light of different wavelengths according to time zones will be described with reference to FIGS. 5 to 7. FIGS. 5 to 7 are drawings illustrating a method for controlling wavelengths of a phototherapy image according to another exemplary embodiment.

According to the current exemplary embodiment, an application processor 200 outputs a phototherapy control signal CONTS to a timing controller 100 according to a current time, thereby displaying light of a specific wavelength on a display unit 130 according to the time.

As shown in FIG. 5, the application processor 200 may output the phototherapy control signal CONTS such that the display unit 130 substantially displays light of an approximate wavelength of 464 nm from 06 hrs. to 17 hrs.

When the phototherapy control signal CONTS is received, the timing controller 100 reads a phototherapy image signal for displaying light of 464 nm wavelength from the memory 140, and may output signals such that when a still image signal is received, the phototherapy image and the still image are mixed and displayed on the display unit 130.

As shown in FIG. 6, the application processor 200 may output the phototherapy control signal CONTS such that the display unit 130 displays light of an approximate wavelength of 440 nm from 20 hrs. to 06 hrs.

When the phototherapy control signal CONTS is received, the timing controller 100 reads the phototherapy image signal for displaying light of 444 nm wavelength from the memory 140, and may output signals such that when the still image signal is received, the phototherapy image and the still image are displayed in mixed manner (e.g., in alternating manner) on the display unit 130.

In addition, as shown in FIG. 7, the application processor 200 may output the phototherapy control signal CONTS such that the display unit 130 displays 464 nm and 440 nm light in spatially alternating manner from 17 hrs. to 20 hrs. Although FIG. 7 shows a pattern of different-wavelength light being displayed in alternating horizontal strips, any pattern of any wavelengths of light is contemplated.

When the phototherapy control signal CONTS is received, the timing controller 100 reads the phototherapy image signal for displaying light of 464 nm wavelength and the phototherapy image signal for displaying light of 440 nm wavelength from the memory 140, and may output signals such that when a still image signal is received, the phototherapy images and the still image are mixed in alternating manner and displayed on the display unit 130.

For example, the phototherapy image frame for displaying light of 464 nm wavelength may be inserted between a first still image frame and a second still image frame, the phototherapy image frame for displaying light of 440 nm wavelength may be inserted between the second still image frame and a third still image frame, the 464 nm phototherapy image frame may be inserted between the third still image frame and a fourth still image frame, and so on.

Alternatively, the timing controller 100 may generate one phototherapy image frame using the phototherapy image signal for displaying light of 464 nm wavelength and the phototherapy image signal for displaying light of 440 nm wavelength. For example, the timing controller 100 may generate the phototherapy image frame for alternately emitting light of the wavelength of 464 nm or 440 nm according to pixel row. In addition, the timing controller 100 may insert the generated phototherapy image between the first and second still image frames.

The present invention may be implemented as a code in a computer readable medium in which a program is recorded. The computer readable medium may include any and all kinds of recording devices in which data readable by a computer system are stored. An example of the computer readable medium may include a hard disk drive (HDD), a solid state disk (SSD), a silicon disk drive (SDD), a read only memory (ROM), a random access memory (RAM), a compact disk read only memory (CD-ROM), a magnetic tape, a floppy disk, an optical data storage, or the like, and may also include a medium implemented in a form of a carrier wave (for example, transmission through the Internet).

In addition, the computer may also include the timing controller 100 of the terminal.

Therefore, the above detailed description is not to be interpreted as being restrictive, but is to be considered as being illustrative. The scope is to be determined by reasonable interpretation of the claims, and all alterations within equivalences fall within the scope. Furthermore, different features of the various embodiments, disclosed or otherwise understood, can be mixed and matched in any manner to produce further embodiments within the scope of the invention.

<Description of Symbols>

| | |
|---|---|
| 100: timing controller | 110: data driver |
| 120: scan driver | 130: display unit |
| 140: memory | 200: application processor |
| 210: user input unit | |

What is claimed is:

1. A display device comprising:
a display unit including a plurality of pixels, wherein each of the plurality of pixels displays an image according to a data signal;
a data driver adapted to select a gray voltage according to an image data signal and transmit the gray voltage as the data signal;
a memory storing a phototherapy image signal for displaying light of a specific wavelength; and
a controller adapted to receive an image signal comprising a plurality of sequential image frames having a time interval between image frames and then, when certain of the image frames are determined by the controller to represent a still image, the controller is adapted to insert a sub-image frame of the phototherapy image signal between immediately successive image frames of the certain of the image frames to generate the image data signal, and output the image data signal to the data driver.

2. The display device of claim 1, wherein the controller is further constructed to separate a first one of the image frames into a plurality of sub-images, to compare the plurality of sub-images with corresponding sub-images of a previous one of the image frames that is received before the first image frame, to detect whether the compared sub-images differ from each other, and to thereby determine whether the image signal represents the still image.

3. The display device of claim 1, wherein the memory storing information corresponding to the specified wavelength of light to be emitted.

4. The display device of claim 3, wherein the controller is further arranged to receive a control signal for controlling insertion of the sub-image frame, and to read the information from the memory according to the control signal.

5. The display device of claim 4, wherein the control signal includes a signal for directing the controller such that the sub-image frame for emitting light of a wavelength corresponding to a specific time zone is displayed.

6. The display device of claim 4, wherein the plurality of image frames includes immediately successive first and second image frames, and the controller is further constructed to insert the sub-image frame such that an interval between the first image frame and the sub-image frame is greater than that between the sub-image frame and the second image frame.

7. The display device of claim 6, wherein the control signal includes a signal directing the controller to selectively read the information corresponding to the specified wavelength.

8. The display device of claim 7, wherein the controller is further constructed to read the information, and to insert ones of the sub-image frames between successive image frames.

9. The display device of claim 7, wherein the controller is further constructed to correct a color of the image signal at least partially according to the specified wavelength of the sub-image frame that is selected by the control signal.

10. The display device of claim 9, wherein the controller is further constructed to correct the color of the image signal at least partially according to a ratio of the interval between the first image frame and the sub-image frame to the interval between the sub-image frame and the second image frame.

11. The display device of claim 9, wherein the memory further stores information corresponding to a color correction matrix for correcting the color of the image signal.

12. A method of controlling a display device, wherein the display device comprises a display unit including a plurality of pixels, wherein each of the pixels displays an image according to a data signal, a data driver adapted to select a gray voltage according to an image data signal and transmit the gray voltage as the data signal, a memory storing a phototherapy image signal for displaying light of a specific wavelength;

and a controller adapted to output the image data signal to the data driver, the method comprising:

receiving, by the controller, an image signal comprising a plurality of sequential image frames having a time interval between image frames;

determining, by the controller, whether the image signal represents a still image;

when certain of the image frames of the image signal are determined to represent a still image, inserting a sub-image frame of the phototherapy image signal between immediately successive image frames of the certain of the image frames to generate the image data signal.

13. The method of claim 12, wherein the determining further includes: separating a first one of the image frames into a plurality of sub-images; and detecting whether the sub-images of successive image frames represent a still image, by comparing the sub-images of the first one of the image frames with the corresponding sub-images of a previous image frame.

14. The method of claim 12, further comprising:
receiving a control signal for controlling insertion of the sub-image frame; and
reading, from the memory, information corresponding to a specified wavelength of light to be emitted according to the sub-image frame.

15. The method of claim 14, wherein the inserting further includes inserting the sub-image frame between successive first and second ones of the image frames so that an interval between the first image frame and the sub-image frame is greater than an interval between the sub-image frame and the second image frame.

16. The method of claim 15, wherein the reading further includes selectively reading the information from the memory.

17. The method of claim 16, further comprising correcting a color of the image signal according to the specified wavelength corresponding to the selectively read information.

18. The method of claim 16, wherein the information corresponds to multiple ones of the specified wavelengths.

19. The method of claim 17, wherein the correcting further includes correcting the color of the image signal at least partially according to a ratio of the interval between the first image frame and the sub-image frame to the interval between the sub-image frame and the second image frame.

20. The method of claim 18, wherein the inserting further includes respectively sequentially inserting multiple ones of the sub-image frames each between two immediately successive image frames.

\* \* \* \* \*